United States Patent [19]

Mauvernay et al.

[11] 4,062,956
[45] Dec. 13, 1977

[54] SUBSTITUTED 2-(2-HYDROXYETHYL)TETRAHYDRO-1,4 OXAZINES AND QUATERNARY SALTS THEREOF USEFUL FOR TREATING SPASMODIC SYNDROMES

[75] Inventors: Roland Yves Mauvernay, Riom; Norbert Busch, La Tourette; Jacques Moleyre, Menetrol; Jacques Simond, Chamalieres; André Monteil, Gerzat, all of France

[73] Assignee: Centre Europeen de Recherches Mauvernay, Riom Cedex, France

[21] Appl. No.: 724,068

[22] Filed: Sept. 16, 1976

[30] Foreign Application Priority Data

Sept. 29, 1975 France .................................. 75.29819

[51] Int. Cl.² .......................... A01N 9/00; A01N 9/22; C07D 265/00; C07D 273/00
[52] U.S. Cl. ............................... 424/248.57; 424/329; 544/171; 544/170
[58] Field of Search .................... 260/244 R, 247.7 Y, 260/247.7 Z; 424/248

[56] References Cited

U.S. PATENT DOCUMENTS 3,658,806  4/1972  Denss et al. ..................... 424/248.54

Primary Examiner—Albert T. Meyers
Assistant Examiner—D. W. Robinson
Attorney, Agent, or Firm—Haseltine, Lake & Waters

[57] ABSTRACT 2-(2-Hydroxyethyl)tetrahydro-1,4-oxazines and quaternary salts thereof having the formula:

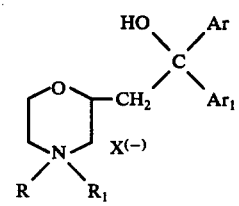

wherein Ar and $Ar_1$ are the same or different and are unsubstituted and substituted aryl, said substituent being a halogen atom, R represents a lower alkyl group having from 1 to 4 carbon atoms, $R_1$ is zero when $X^{(-)}$ is zero or is an alkyl group of from 1 to 4 carbon atoms which is the same or different from R, as defined above, and $X^{(-)}$ is zero when $R_1$ is zero or is selected from the group consisting of $Cl^{(-)}$, $Br^{(-)}$, $I^{(-)}$ and $CH_3SO_4^{(-)}$ when $R_1$ is lower alkyl, as defined above, is described. These compounds are useful for treating spasmodic syndromes.

8 Claims, No Drawings

SUBSTITUTED 2-(2-HYDROXYETHYL)TETRAHYDRO-1,4 OXAZINES AND QUATERNARY SALTS THEREOF USEFUL FOR TREATING SPASMODIC SYNDROMES

BACKGROUND OF THE INVENTION

1. Field of the Invention

The present invention relates to novel substituted 2-(2-hydroxyethyl)tetrahydro-1,4oxazines as well as to their quaternary derivatives useful in human therapeutics for the treatment of spasmodic syndromes. The invention relates also to a process for obtaining these compounds and to the application of said quaternary derivatives to the treatment of spasmodic syndromes of the smooth muscle.

2. Description of the Prior Art

A large number of aminoalchohol derivatives are known possessing spasmolytic properties (Ehrhart-/Ruschig Arzneimittel II p. 75-97).

These spasmolytic properties are coupled either with an anticholinergic action or with a musculotropic action.

OBJECTS AND GENERAL DESCRIPTION OF THE INVENTION

The quaternary derivatives of the 2-(2-hydroxyethyl)tetrahydro-1,4 oxazines according to the present invention possess markedly and simultaneously both antichorlinergic and musculotropic actions. They correspond to the following general structural formula:

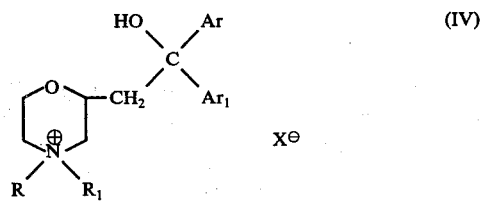

In this formula the substituents have the following significance:

Ar and $Ar_1$, which can be the same or different, represent aromatic residues, such as phenyl nuclei, which can be substituted by a halogen atom or unsubstituted;

R and $R_1$, can be the same or different, represent a lower alkyl group having 1 to 4 carbon atoms; and $X^{31}$ is an anion of the type $Cl^-$, $Br^-$, $I^-$ or $CH_3SO_4^-$.

The present invention also relates to the substituted 2-(2-hydroxyethyl)tetrahydro-1,4 oxazines themselves, notably useful as intermediates in the synthesis of the compounds of formula IV.

The invention also relates to a process for producing these compounds.

The compounds according to the invention are synthesised from 2-cyanomethyl tetrahydro-1,4 oxazines whose preparation has been described by applicants in French patent application No 74 16 331 of 10 May 1974. These starting compounds correspond to the general formula:

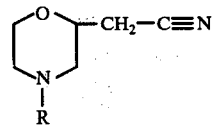

in which R has the same significance as indicated above. A derivative of this type can be easily converted by the action of HCl in an Et OH medium, then hydrolysed and treated with anhydrous $NH_3$, into the corresponding ester, passing through the intermediate stage of the imino-ester which is not necessary to isolate.

One of these esters is then reacted with at least one organomagnesium compound of the type Ar—MgX' or $Ar_1$—MgX' in a solvent such as ethyl ether, Ar (or $Ar_1$) having the above-indicated significance and X' being a halogen atom.

The compounds thus obtained can serve as intermediates in syntheses. For example, it is possible to react them with a reactant of the type $R_1$-X to obtain the corresponding quaternary ammonium salts, whose pharmacological properties justify their use in medicine for the treatment of spasmodic conditions.

The process of synthesis may be shown schematically as follows:

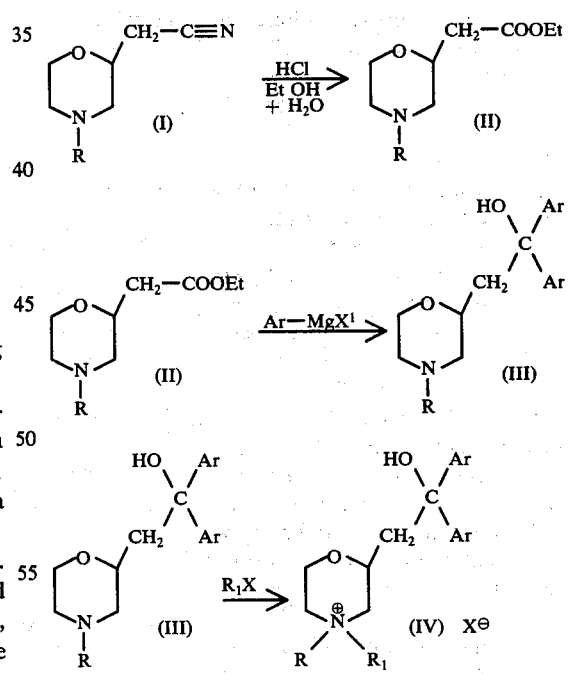

DESCRIPTION OF PREFERRED EMBODIMENTS

The invention is described in more detail in the following Examples, given purely by way of illustration and which are not to be regarded as defining the invention in any way.

EXAMPLE 1

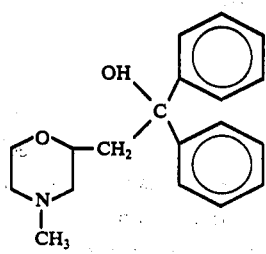
(Compound 1)

In a first step, 2-carbethoxy-methyl 4-methyl tetrahydro-1,4 oxazine of the formula

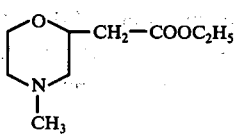

is synthesised.

For this purpose:

70 g of 2-cyanomethyl tetrahydro-1,4 oxazine are dissolved in 1000 ml of absolute ethanol. This solution is saturated at −10° C with anhydrous HCl gas.

20 ml of water are then added and it is refluxed for 1 hour.

After having driven off the solvent, the residue is taken up with 400 ml of anhydrous chloroform and the solution is treated with a current of anhydrous $NH_3$.

The precipitated $NH_4Cl$ is filtered off. The solvent is distilled and the residue is rectified under vacuum, to obtain 52 g of the above ethyl ester.

$BP_{12} = 108°$ C
$N_D^{23°} = 1,4480$

Under the usual conditions, a solution of phenylmagnesium bromide in anhydrous ethyl ether is prepared, from 7.2 g of magnesium turnings, 47.1 g (0.3 M) of bromobenzene and 100 ml of anhydrous ether. 18.7 g (0.1 M) of 2-carbethoxy-methyl 4-methyl tetra-hydro-1,4-oxazine are added with vigorous stirring, gradually, so as to keep the solvent refluxing. After the addition, refluxing is continued for 3 hours.

It is hydrolysed under the usual conditions with a saturated solution of $NH_4Cl$. The decanted organic phase is extracted with an aqueous solution of ∼ 4N HCl. The aqueous solution is washed with ether then made alkaline with $Na_2CO_3$. The product crystallises. After recrystallisation from anhydrous ether, 10.5 g of compound 1 are obtained.

MP = 110° C

Its hydrochloride, obtained by treating a solution of the base in absolute Et OH with anhydrous HCl gas, has a melting point MP = 212° C and has the following analytical characteristics:

| (where M = 333.88) | C % | H % | N % | HCl % |
|---|---|---|---|---|
| Calculated | 68.35 | 7.24 | 4.19 | 10.92 |
| Found | 68.14 | 7.26 | 4.13 | 10.91 |

EXAMPLE 2

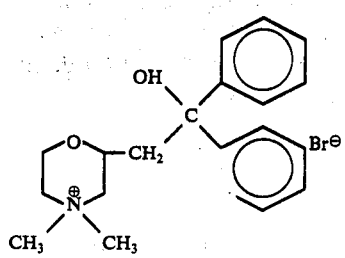
(Compound no2)

A solution of 5 g of Compound 1 in 50 ml of pure acetone is treated with 5 g of methyl bromide. After some hours, the product crystallises. After draining, it is recrystallised in absolute Et OH.

5 g of product are thus obtained.

MP = 233° C.

| Analysis for M = 392.35 | C % | H % | N % | Br % |
|---|---|---|---|---|
| Calculated | 61.22 | 6.67 | 3.57 | 20.36 |
| Found | 61.31 | 6.73 | 3.41 | 19.93 |

EXAMPLE 3

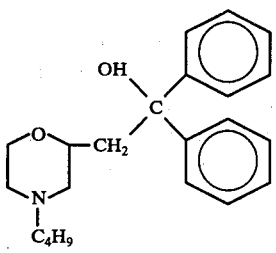
(Compound 3)

16 g of Compound 3 are obtained by operating under the same conditions as those described for compound 1, starting from 22.9 g (0.1 M) of 2-carbethoxy-methyl 4-n-butyl tetrahydro-1,4 oxazine, prepared as described in the Example 1, but replacing the absolute ethanol by n-butanol. Melting point of the hydrochloride MP = 211° C

| Analysis of the hydrochloride (for M = 375.94) | C % | H % | N % | HCl % |
|---|---|---|---|---|
| Calculated | 70.29 | 8.04 | 3.72 | 9.70 |
| Found | 71.00 | 7.97 | 3.63 | 9.64 |

EXAMPLE 4

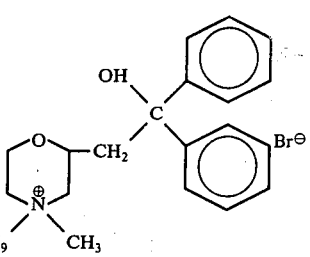
(Compound 4)

2 g of Compound 3 in 50 ml of pure acetone are treated with 2 g of methyl bromide. The cristals obtained are recrystallised from absolute EtOH.

In this way 2.5 g of Compound 4 are obtained.
MP = 244° C

| Analysis (for M = 4.33.42) | C % | H % | N % |
|---|---|---|---|
| Calculated | 63.74 | 7.21 | 3.23 |
| Found | 64.01 | 7.38 | 3.17 |

EXAMPLE 5

(compound 5)

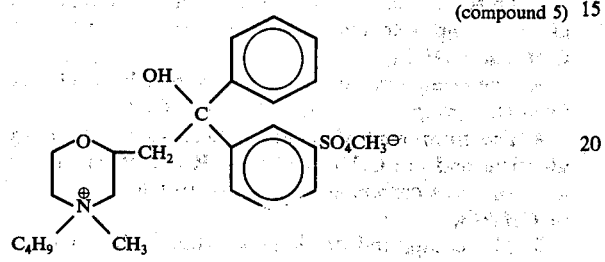

5 g of the Compound 3 in 50 ml of acetone were treated with 2 g of freshly distilled methyl sulfate. After 12 hours the solvent was driven off. The residue was treated with ethyl acetate. 4.5 g of Compound 5 were thus obtained.
MP = 165° C.

| Analysis (for M = 449.62) | C % | H % | N % |
|---|---|---|---|
| Calculated | 61.44 | 7.85 | 3.11 |
| Found | 61.18 | 7.63 | 2.93 |

EXAMPLE 6

(Compound 6)

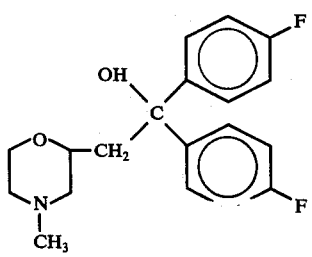

Under similar conditions to those described in Example 1, from 7.2 g of magnesium, with 52.5 g (0.3 M) of 4-fluoro bromobenzene, 100 ml of anhydrous ether and 18.7 g of 2-carbethoxy-methyl 4-methyl tetrahydro-1,4 oxazine, 16.7 g of Compound 6 were obtained.

Melting point of the hydrochloride: 128° C (hygroscopic)

| Analysis of the hydrochloride (M = 369.85) | C % | H % | N % | HCl % |
|---|---|---|---|---|
| Calculated | 61.70 | 5.99 | 3.79 | 9.86 |
| Found | 61.57 | 5.82 | 3.75 | 9.80 |

EXAMPLE 7

(Compound 7)

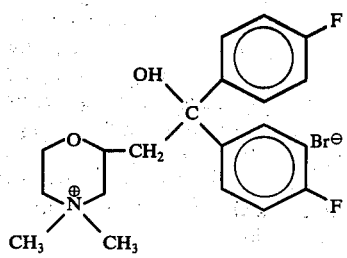

5 g of the Compound 6 in 60 ml of pure acetone were treated with 4.5 g of methyl bromide. After recrystallisation in anhydrous isopropanol, 4.8 g of the product were obtained.
MP = 134° C (hygroscopic)

| Analysis (M = 428.33) | C % | H % | N % | Br % |
|---|---|---|---|---|
| Calculated | 56.08 | 5.65 | 3.27 | 18.66 |
| Found | 56.15 | 5.62 | 3.13 | 19.00 |

Pharmacological tests

The pharmacological studies of the compounds according to the invention were directed essentially to the elucidation of the antispasmodic potentialities of the cations, particularly at the level of smooth muscle spasms induced by acetylcholine, histamine and Ba++ ions. These investigations were carried out in vitro according to the technique of MAGNUS (Pflug. Arch. Ges. Physiol. 1904, 102, 349, and 1904, 103, 515 and 525) by using as biological indicators the jejunum of the rat for the first agonist and the ileum of the guinea pig for the two other agonists. The isolated organs were kept alive in a thermostatic oxygen Tyrode solution at 30° C and their contractions were recorded.

The response curve line as a function of the dose enabled the calculation of the affinity parameters ($pA_2$ and $pD'_2$) of the compounds according to the invention for the different types of receptor (VAN ROSSUM J.M. - Arch. Int. Pharmacodyn. 1963, 143, 299 –330).

The results obtained with the compounds according to the invention and two conventional compounds taken as references are given in Table I below:

TABLE I

| COMPOUNDS | AGONISTS | ACETYLCHOLINE | | HISTAMINE | | Ba++ | | TYPE OF ANTAGONIST EXERTED |
|---|---|---|---|---|---|---|---|---|
| | | $pA_2$ | $pD'_2$ | $pA_2$ | $pD'_2$ | $pA_2$ | $pD'_2$ | |
| 2 | | 6.7 | — | 5.20 | — | 4.90 | — | Competitive |
| 7 | | 5.46 | 3.21 | 5 | 3.70 | 5.87 | 4.04 | Dualist |
| Tiemonium | | .7 | — | 5.21 | — | 4.95 | — | Competitive |
| Papaverine | | — | 5.03 | — | 4.98 | — | 4.78 | Non competitive |

These results interpreted by the principles of molecular pharmacology developed by ARIENS et Al. (Medicinal chemistry (Molecular pharmacology), 1, 119 – 286), show a great similarity of mechanism and intensity of action between compound no 2 and Tiemonium and for compound no 7 a mechanism of action which brings into play at the same time the competitive mechanism of Tiemonium and the non-competitive mechanism of papaverine.

To the knowledge of applicants, this dualism of activity is unknown for any other antispasmodic agent.

These pharmacological results therefore enable the application of these compounds to be envisaged in human therapeutics for the treatment of all spasmodic syndromes of the smooth muscle, whether of vascular, digestive or bronchial origin. The compounds could be administered in customary pharmaceutical forms at daily dosages comprised between 10 and 500 mg according to the route of administration, of the active compound. The active compound may be associated with the usual pharmaceutical excipients or vehicles for the provision of dosage units.

We claim:
1. A compound selected from the group consisting of 2-(2-hydroxyethyl)tetrahydro-1,4-oxazines of the formula:

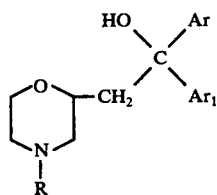

wherein Ar and $Ar_1$ are the same or different and are selected from the group consisting of unsubstituted and substituted aryl, said substituent being a halogen atom, R is lower alkyl having from 1 to 4 carbon atoms; and the quaternary salts thereof having the formula:

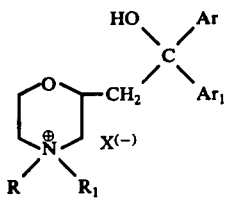

wherein Ar, $Ar_1$ and R are as defined above and $R_1$ is lower alkyl having from 1 to 4 carbon atoms and $X^{(-)}$ is selected from the group consisting of $Cl^{(-)}$, $Br^{(-)}$, $I^{(-)}$ and $CH_3SO_4(-)$.

2. The compound of claim 1, wherein Ar and $Ar_1$ are identical and selected from the group consisting of $C_6H_5$ and $C_6H_4F$.

3. The compound of claim 1, wherein R is selected from the group consisting of $CH_3$ and $C_4H_9$.

4. The compound of claim 1, wherein Ar and $Ar_1$ are identical and are $C_6H_5$ or $C_6H_4F$; R and $R_1$ are lower alkyl of 1 to 4 carbon atoms and $X^{(-)}$ is $Cl^{(-)}$, $Br^{(-)}$, $I^{(-)}$ or $CH_3SO_4^{(-)}$.

5. The compound of claim 4, wherein R is $CH_3$ or $C_4H_9$.

6. The compound of claim 4 wherein $R_1$ is $CH_3$.

7. Pharmaceutical composition for the treatment of spasmodic syndromes, notably of the smooth muscle, comprising an anti-spasmolytic effective amount of a compound of claim 1 and a pharmaceutically acceptable carrier.

8. A method of treating spasmodic syndromes, notably of the smooth muscle, comprising administering to a patient having said spasmodic syndromes a daily amount of from 10 to 500 mg of an antispasmolytic compound of claim 1.

* * * * *